United States Patent [19]

Geller et al.

[11] 3,954,975
[45] May 4, 1976

[54] SALTS OF ACTH-PEPTIDES AND PROCESSES FOR THEIR MANUFACTURE

[75] Inventors: Leo Geller, Riehen; Werner Rittel, Basel, both of Switzerland

[73] Assignee: Ciba-Geigy Corporation, Ardsley, N.Y.

[22] Filed: July 10, 1974

[21] Appl. No.: 487,093

Related U.S. Application Data

[62] Division of Ser. No. 331,148, Feb. 9, 1973, abandoned.

[30] Foreign Application Priority Data

Feb. 17, 1972 Switzerland.......................... 2300/72

[52] U.S. Cl. ................................................ 424/179
[51] Int. Cl.² ................ A61K 37/40; C07C 103/52
[58] Field of Search................. 260/112.5; 424/179, 424/177

[56] References Cited

UNITED STATES PATENTS

| 3,228,839 | 1/1966 | Kappeler et al. ................... 424/179 |
| 3,503,951 | 3/1970 | Iselin et al. ....................... 260/112.5 |
| 3,632,743 | 1/1972 | Geller et al. ....................... 260/112.5 |
| 3,639,383 | 2/1972 | Geller............................... 260/112.5 |
| 3,755,286 | 8/1973 | Riniker et al. .................... 260/112.5 |
| 3,761,459 | 9/1973 | Pless et al. ........................ 260/112.5 |
| 3,761,461 | 9/1973 | Pless et al. ........................ 260/112.5 |
| 3,770,715 | 11/1973 | Tesser et al...................... 260/112.5 |

*Primary Examiner*—Lewis Gotts
*Assistant Examiner*—Reginald J. Suyat
*Attorney, Agent, or Firm*—Joseph G. Kolodny; John J. Maitner; Theodore O. Groeger

[57] ABSTRACT

Pharmaceutical preparations containing acid addition salts of ACTH-peptides with saturated or unsaturated fatty acids of chain length 12–36 carbon atoms.

13 Claims, No Drawings

SALTS OF ACTH-PEPTIDES AND PROCESSES FOR THEIR MANUFACTURE

CROSS-REFERENCE TO RELATED APPLICATION

The present application is a division of our application Ser. No. 331,148, filed Feb. 9, 1973 (now abandoned).

In the therapeutic application of ACTH-peptides a problem which has not yet been solved satisfactorily is that the peptides are inactivated too rapidly in the body. Attempts have been made in various ways to extend the activity, for example by forming complexes of the peptides with inorganic substances such as sparingly soluble zinc compounds, for example zinc hydroxide or zinc phosphate, or with organic substances such as gelatine, polyvinylpyrrolidone, phosphoric acid esters of polyphenols or polyalcohols, for example polyphloretin phosphate, or alkaline or acid polyaminoacids, for example protamine or polyglutamic acids. Apart from the fact that the achieved prolongation of the action is not entirely satisfactory, certain of the preparations manufactured also show the disadvantage that they can cause allergies.

It has now been found that a substantially stronger prolongation of the action than hitherto can be achieved if the peptides are employed in the form of sparingly water-soluble acid addition salts with long-chain fatty acids, preferably in a liquid fatty acid ester, especially a vegetable oil, it also being possible for the peptide salt to be adsorbed on a carrier, above all an aluminium salt of a higher fatty acid, or in a gel which consists of a mixture of approx. 0.1 to 5%, preferably 0.5 to 2%, of a fatty acid salt of aluminum and a liquid fatty acid ester, as described in Swiss application No. 2,299/72 (Case 4-8023), or by suspending the sparingly soluble or insoluble salts in aqueous solution.

Hence the subject of the present invention are sparingly water-soluble acid addition salts of ACTH-peptides and long-chain fatty acids, and processes for their manufacture. A further subject of the invention is the application of ACTH-peptides in the form of their sparingly water-soluble fatty acid addition salts. In particular, the invention also relates to the manufacture and use of ACTH-peptides in the form of oily solutions or oily or aqueous suspensions which contain an acid addition salt of the peptide and a fatty acid.

The new ACTH preparations prepared with salts of fatty acids show a prolongation of the action of several days, for example 3–7 days. This was in no way foreseeable from the state of the art. It is also surprising, above all, that this action can be achieved with the customary extremely small doses of peptide, for example even with fractions of a milligram.

The description of ACTH-peptides is applied to the natural ACTH-peptides and to synthetic peptides or peptide-amides having an aminoacid sequence which is shorter and/or modified with respect to certain aminoacids. For example, ACTH-active peptides or peptide-amides to be mentioned are those with a N-terminal sequence up to aminoacid 16 to 39 of the natural corticotropins. In this sequence, one or more of the aminoacids, above all of the aminoacids 1 to 4, can be absent as is shown, for example, in Angew. Chemie 83, 155 (1971), or one or more aminoacids, for example in the positions 1–5, 11, 15–18 and 25–33, can be replaced by other aminoacids, and aminoacid 1 can also be replaced by a desaminocarboxylic acid. Thus, for example, the serine radicals serine$^1$ and/or serine$^3$ can be replaced by glycine or alanine, tyrosine$^2$ can be replaced by phenylalanine, methionine$^4$ can be replaced by an α-amino-lower alkylacetic acid, wherein lower alkyl possesses 2–4 carbon atoms, for example norvaline, valine, norleucine, leucine, isoleucine and α-aminobutyric acid, glutamic acid$^5$ can be replaced by glutamine, lysine$^{11}$ and/or lysine$^{15,16}$ can be replaced by ornithine, arginine$^{17,18}$ can be replaced by lysine or ornithine, and aminoacid$^{25}$ can be replaced by valine. Serine$^1$ can also be replaced, for example, by proline, α- or β-alanine, threonine, propionic acid or β-aminopropionic acid, β-hydroxypropionic acid, butyric acid, γ-aminobutyric acid, α-aminoisobutyric acid, valeric acid, caproic acid, ε-aminocaproic acid or phenylglycine. All aminoacids apart from those in the N-terminal 1-position necessarily have the L-configuration. Preferably, the new salts are derived from ACTH-active peptides of which the first aminoacid has the D-configuration, above all D-serine; furthermore, salts of peptides with a chain length of 18–24 aminoacids, above all with 18 aminoacids, are preferably used. The peptides can in particular also be present as C-terminal N-unsubstituted amides. Fatty acid salts of peptides with a sequence of 18 aminoacids, above all D-Ser$^1$-Lys$^{17,18}$-β$^{1-18}$-corticotropin-Lys$^{18}$-amide are preferred. Peptides with 25–39 aminoacids preferably have, in the 25–33 range, the sequence found for human ACTH (compare Nature New Biology 235, 114 [1972]).

Further examples to be mentioned as the peptide base for the fatty acid salts are D-Ser$^1$-corticotropin-Arg$^{18}$-amide, D-Ser$^1$-Orn$^{11}$-Lys$^{17,18}$-β$^{1-18}$-corticotropin-Lys$^{18}$-amide, D-Ser$^1$-Orn$^{11,15-18}$-β$^{1-18}$-corticotropin-Orn$^{18}$-amide, α-aminoisobutyryl$^1$-β$^{1-18}$-corticotropin-Arg$^{18}$-amide, D-Ser$^1$-Orn$^{17,18}$-β$^{1-18}$-corticotropin-Orn$^{18}$-amide, D-Ser$^1$-Gly$^3$-Lys$^{17,18}$-β$^{1-18}$-corticotropin-Lys$^{18}$-amide, D-Ser$^1$-Nle$^4$-Lys$^{17,18}$-β$^{1-18}$-corticotropin-Lys$^{18}$-amide, D-Ser$^1$-Lys$^{17,18}$-β$^{1-18}$-corticotropin, β$^{1-19}$-corticotropin, D-Ser$^1$-β$^{1-19}$-corticotropin, β$^{1-19}$-corticotropin-Pro$^{19}$-amide, Glu(NH$_2$)$^5$-β$^{1-19}$-corticotropin, D-Ser$^1$-Lys$^{17,18}$-Val$^{19}$-β$^{1-19}$-corticotropin-Val$^{19}$-amide, D-Ser$^1$-Nle$^4$Lys$^{17,18}$-Val$^{19}$-β$^{1-19}$-corticotropin-Val$^{19}$-amide, β$^{1-20}$-corticotropin-Val$^{20}$-amide, D-Ser$^1$-β$^{1-20}$-corticotropin-Val$^{20}$-amide, D-Ser$^1$-Lys$^{17,18}$-β$^{1-20}$-corticotropin-Val$^{20}$-amide, α-aminobutyryl$^4$-Glu(NH$_2$)$^5$-β$^{1-20}$-corticotropin-Val$^{20}$-amide, D-Ser$^1$-Lys$^{17,18}$-β$^{1-19}$-corticotropin-Pro$^{19}$-amide, α-aminobutyryl$^4$-β$^{1-20}$-corticotropin-Val$^{20}$-amide, β$^{1-21}$-corticotropin, D-Ser$^1$-Lys$^{17,18}$-β$^{1-21}$-corticotropin-Lys$^{21}$-amide, D-Ser$^1$-Lys$^{17,18}$-β$^{1-22}$-corticotropin-Val$^{22}$-amide, β$^{1-23}$-corticotropin, β$^{1-23}$-corticotropin-Tyr$^{23}$-amide, β-Ala$^1$-β$^{1-23}$-corticotropin-Tyr$^{23}$-amide, D-Ser$^1$-β$^{1-23}$-corticotropin-Tyr$^{23}$-amide, D-Ser$^1$-Ala$^3$-β$^{1-23}$-corticotropin-Tyr$^{23}$-amide, Gly$^1$-β$^{1-23}$-corticotropin-Tyr$^{23}$-amide, D-Ser$^1$-Lys$^{17,18}$-β$^{1-23}$-corticotropin-Tyr$^{23}$-amide, β$^{1-24}$-corticotropin, Glu(NH$_2$)$^5$-β$^{1-24}$-corticotropin, D-Ser$^1$-Orn$^{17,18}$-β$^{1-24}$-corticotropin, Gly$^{1,3}$-β$^{1-24}$-corticotropin, Orn$^{17,18}$-β$^{1-24}$-corticotropin, Lys$^{17,18}$-β$^{1-24}$-corticotropin, D-Ser$^1$-Nle$^4$-β$^{1-24}$-corticotropin, D-Ser$^1$-β$^{1-24}$-corticotropin, D-Ala$^1$-β$^{1-24}$-corticotropin, D-Ser$^1$-Gly$^3$-Lys$^{17,17}$-β$^{1-24}$-corticotropin, D-Ser$^1$-Nle$^4$-Lys$^{17,18}$-β$^{1-24}$-corticotropin-Pro$^{24}$-amide, D-Ser$^1$-Orn$^{17,18}$-β$^{1-24}$-corticotropin-Pro$^{24}$-amide, D-Ser$^1$-Nle$^4$-Orn$^{17,18}$-β$^{1-24}$-corticotropin-Pro$^{24}$-amide, D-Ser$^1$-Gly$^3$-Lys$^{17,18}$-β$^{1-24}$-corticotropin-Pro$^{24}$-amide, D-Ser$^1$-Lys$^{17,18}$-β$^{1-24}$-corticotropin, D-Ser$^1$-Lys$^{17,18}$-β$^{1-24}$-corticotropin-Pro$^{24}$-amide, D-Ser$^1$-Nle$^4$-Val$^{25}$-β$^{1-25}$-corticotropin-Val$^{25}$-amide, D-Ser$^1$-Nle$^4$-D-Val$^{25}$-β$^{1-25}$-corticotropin-D-Val$^{25}$-amide, D-Ser$^1$-Nva$^4$-Lys$^{17,18}$-Val$^{25}$-β$^{1-25}$-corticotropin-Val$^{25}$-amide, $\beta^{1-25}$-corticotropin-Val$^{25}$-amide, D-Ser$^{1}$-Nle$^{4}$-Lys$^{17,18}$-Val$^{25}$-$\beta^{1-25}$-corticotropin-Val$^{25}$-amide, Nle$^{4}$-Val$^{25}$-$\beta^{1-25}$-corticotropin-Val$^{25}$-amide, Nva$^{4}$-Val$^{25}$-$\beta^{1-25}$-corticotropin-Val$^{25}$-amide, Nle$^{4}$-Lys$^{17,18}$-Val$^{25}$-$\beta^{1-25}$-corticotropin-Val$^{25}$-amide, $\beta^{1-26}$-corticotropin, $\beta^{1-28}$-corticotropin, $\beta^{1-30}$-corticotropin, $\beta^{1-31}$-corticotropin, $\beta^{1-39}$-corticotropin, D-Ser$^{1}$-$\beta^{1-39}$-corticotropin, Gly$^{1}$-$\beta^{1-39}$-corticotropin, $\alpha_h^{1-39}$-corticotropin and D-Ser$^{1}$-$\alpha_h^{1-39}$-corticotropin.

Possible fatty acids for the manufacture of the sparingly water-soluble salts of fatty acids which have been mentioned are long-chain saturated or unsaturated fatty acids with 12–36 carbon atoms, preferably saturated fatty acids with 18–22 carbon atoms, for example lauric acid, tridecylic acid, myristic acid, pentadecylic acid, palmitic acid, margaric acid, stearic acid, nonadecylic acid, arachidic acid, eicosa-1-carboxylic acid, behenic acid, lignoceric acid (tetracosylic acid), cerotic acid (hexacosylic acid), montan acid (octacosylic acid), melissic acid (triacontylic acid), lacceric acid (dotriacontylic acid), gheddic acid (tetratriacontylic acid), ceroplastic acid (pentatriacontylic acid), hexatriacontylic acid and corresponding unsaturated acids such as, for example, oleic acid, elaidic acid, erucic acid, brasidic acid and linoleic acid. The peptide acid addition salt contains the number of fatty acid radicals corresponding to the number of basic groups (without histidine) minus the number of the acid groups.

The fatty acid salts of peptides are manufactured in a manner which is in itself known for the manufacture of peptide acid addition salts. Thus, the peptide, or advantageously, a water-soluble acid addition salt of the peptide, above all the acetic acid salt, in a hydrophilic solvent or solvent mixture, can be mixed with the fatty acid or an alkali metal salt thereof, advantageously dissolved in a hydrophilic solvent and the sparingly soluble fatty acid salt can be separated off in a known manner, for example by filtration or by evaporation of the solvent or solvent mixture and, if appropriate, lyophilisation. As hydrophilic solvents there should above all be mentioned optionally substituted water-soluble alcohols such as lower alkanols with 1-4 carbon atoms, above all ethanol, isopropanol and trifluoroethanol, and also dimethylsulphoxide, dimethylformamide and glacial acetic acid. Mixtures of the organic solvent and water are preferred.

As already mentioned, the fatty acid salts can be adsorbed on a solid carrier, especially on a fatty acid salt of aluminium.

The adsorbate of the peptide on the fatty acid salt of aluminium can be manufactured in various ways. Thus, the peptide can be dissolved or suspended in an aqueous or organic solvent, such as water, alcohols or acetone, preferably a solvent which is easily removable by evaporation, for example a lower alkanol such as ethanol or isopropanol, but especially methanol, the fatty acid salt of aluminium can be added and the solvent can be removed from the suspension thus obtained, for example by evaporation in vacuo.

It is however also possible to produce a colloidal solution of the fatty acid salt of aluminium in an organic solvent, for example unsubstituted or chlorinated hydrocarbons such as benzene, chloroform, methylene chloride or ethylene chloride, to suspend the peptide in this colloidal solution and then to remove the solvent by lyophilisation or evaporation. If lyophilisation is carried out, a structured adsorbate is obtained.

The ratio of the amounts of peptide to fatty acid salt of aluminium as the adsorbent is in particular 1:2 to 1:20, preferably 1:5 to 1:10.

In the manufacture of pharmaceutical preparations in the form of oily solutions or suspensions which contain fatty acid salts of ACTH-peptides, the oily solvent or suspending agent used is either a gel, such as is described in Swiss application No. 2,299/72 (Case 4-8023), or, in particular in the case of peptide salt adsorbates, a liquid fatty acid ester (oil) which possesses, as the acid component, a long-chain fatty acid with 8–36, especially 12-22, carbon atoms, such as, for example, the abovementioned fatty acids. The alcohol component of the ester preferably has at most 6 carbon atoms and is a monohydric or polyhydric, for example monohydric, dihydric or trihydric, alcohol, for example methanol, ethanol, propanol, butanol or pentanol or their isomers, but above all glycol or glycerine. Hence, examples of fatty acid esters to be mentioned are: ethyl oleate, isopropyl myristate, isopropyl palmitate, "Labrafil M 2,735" (polyoxyethylene-glycerine trioleate of Messrs Gattefossé, Paris, "Miglycol 812" (triglyceride of saturated fatty acids of chain length $C_8$ to $C_{12}$, of Messrs. Chemische Werke Witten/Ruhr, Germany), but especially vegetable oils such as cottonseed oil, almond oil, olive oil, castor oil, sesame oil, soya bean oil and rape oil, but above all groundnut oil.

To manufacture oily solutions or suspensions, the fatty acid peptide salt, if desired adsorbed on a carrier, is mixed with an oil or an oily gel, such as described in Swiss application No. 2,299/72 (Case 4-8023). An example of a possible procedure for this is to micronize the requisite dose of the peptide salt or peptide salt adsorbate, for example to a particle size of at most $50\mu$ and preferably less than $20\mu$, triturate it with a small amount of the oil or gel and dilute the resulting concentrate thereafter with the remaining oil or gel; alternatively, the peptide salt can be dissolved in a pharmaceutically acceptable solvent or preservative, for example benzyl alcohol or, preferably, tert. chlorobutanol, and can then be mixed with the oil or gel.

To manufacture aqueous suspensions, the fatty acid salt of peptide micronised as above is mixed with aqueous media, preferably physiological sodium chloride solution, aqueous mannitol solution or some other suitable aqueous injection medium and optionally a preservative, for example benzyl alcohol, in optional sequence.

The injection preparations are prepared under anti-microbial conditions. Here, a possible procedure is to subject the active substances and auxiliaries to a suitable anti-microbial treatment before filling into containers. The filling of the germ-free preparations into suitable containers, and the closing, are also carried out under anti-microbial conditions.

The active dose of the peptide to be used in the preparations is the individual dose which is usually administered when employing the peptide in the form of aqueous suspensions or solutions. This dose is, for example, about 0.1 to 3.0 mg/ml.

The examples which follow serve to illustrate the invention.

EXAMPLE 1

200 mg of D-Ser$^{1}$-Lys$^{17,18}$-$\beta^{1-18}$-corticotropin-Lys$^{18}$-amide hexaacetate hydrate are dissolved in 24 ml of ethanol and 1.6 ml of water, and thereafter a solution of 88 mg of lauric acid in 10 ml of ethanol is added. The mixture is evaporated to dryness, the residue is dried overnight in vacuo over sodium hydroxide and is then dissolved in 25 ml of tert. butanol and 5 ml of water whilst warming, the solution is filtered and the filtrate is lyophilized. The residue is again dried in vacuo over sodium hydroxide. 265 mg of lauric acid salt are obtained as a light powder. The solubility of the product in water at 24°C is less than 0.1% (acetic acid salt > 10%).

EXAMPLE 2

The procedure of Example 1 is followed, using a solution of 100 mg of myristic acid in 10 ml of ethanol. 231 mg of myristic acid salt are obtained as a light powder. Its solubility in water at 24°C is less than 0.1%.

EXAMPLE 3

The procedure of Example 1 is followed using a solution of 113 mg of palmitic acid in 12 ml of ethanol. 304 mg of palmitic acid salt are obtained as a colorless light lyophilisate. The solubility in water at 24°C is less than 0.1%.

EXAMPLE 4

The procedure of Example 1 is followed, using a solution of 149 mg of behenic acid in 15 ml of fine spirit. Hereupon, immediate precipitation of the behenic acid salt occurs. It is filtered off, rinsed with a fine spirit-water (19:1) mixture and dried in vacuo over sodium hydroxide. 330 mg of a solid, water-insoluble powder of melting point 141°–146°C are obtained.

EXAMPLE 5

The procedure of Example 1 is followed, using a solution of 124 mg of stearic acid in 12 ml of ethanol. 300 mg of stearic acid salt are obtained as a water-insoluble powder.

EXAMPLE 6

200 mg of D-Ser$^1$-Lys$^{17,18}$-$\beta^{1-19}$-corticotropin pentaacetate hydrate are dissolved in 24 ml of ethanol and 2 ml of water and thereafter a solution of 110 mg of stearic acid in 11 ml of ethanol is added. The mixture is then worked up as described in Example 1. 290 mg of the stearic acid salt of the nonadecapeptide are obtained as a light, colorless lyophilisate which is sparingly soluble in water.

EXAMPLE 7

The procedure indicated in Example 1 is followed, using 200 mg of D-Ser$^1$-Lys$^{17,18}$-$\beta^{1-19}$-corticotropin pentaacetate hydrate and 70 mg of lauric acid. 245 mg of laurate are obtained as a light lyophilisate.

EXAMPLE 8

500 mg of D-Ser$^1$-Gly$^3$-Lys$^{17,18}$-$\beta^{1-18}$-corticotropin-Lys$^{18}$-amide hexaacetate hydrate are dissolved in 100 ml of fine spirit by adding 10 ml of water, a solution of 310 mg of stearic acid in 30 ml of fine spirit is then added and the mixture is evaporated to dryness. The residue is dried for 24 hours in vacuo over sodium hydroxide and dissolved in a tert. butanol-water (4:1) mixture whilst warming, and the solution is lyophilised. The residue is again dried in vacuo over sodium hydroxide. 735 mg of lyophilisate which is practically insoluble in water are obtained.

EXAMPLE 9

The procedure described in Example 4 is followed, but using 200 mg of D-Ser$^1$-Gly$^3$-Lys$^{17,18}$-corticotropin-Lys$^{18}$-amide hexaacetate hydrate, and approx. 200 mg of behenate are obtained as a solid powder which cannot be dissolved in water.

EXAMPLE 10

1 g of Synacthen ($\beta^{1-24}$-corticotropin hexaacetate hydrate) is dissolved in 150 ml of fine spirit and 15 ml of water. A solution of 465 mg of stearic acid in 50 ml of fine spirit is then added, the mixture is evaporated, the residue is dried in vacuo over sodium hydroxide and is thereafter dissolved in a tert.-butanol-water (4:1) mixture whilst warming, and the solution is lyophilized. The residue is dried in vacuo over sodium hydroxide and 1.25 g of the stearic acid salt of the tetracosapeptide are obtained as a sparingly water-soluble powder.

EXAMPLE 11

1.0 g of $\beta^{1-24}$-corticotropin hexaacetate hydrate is dissolved in 15 ml of water, 150 ml of fine spirit are added and a solution, prepared warm, of 560 mg of behenic acid in 60 ml of fine spirit is added. The flocculent precipitate is filtered off after standing for 18 hours at 2°C and is washed with a fine spirit-water (15:1) mixture and dried in vacuo over sodium hydroxide. 1.05 g of behenate are obtained as a water-insoluble powder of melting point 146°-225°C (decomposition).

EXAMPLE 12

A suspension in groundnut oil, which contains, per ml, 2% of benzyl alcohol and 0.5 mg of behenate of D-Ser$^1$-Lys$^{17,18}$-$\beta^{1-18}$-corticotropin-Lys$^{18}$-amide is prepared in the usual manner under anti-microbial conditions. The suspension is homogenised to a particle size of less than 20$\mu$.

In doses of 0.1 mg/kg in rats, on subcutaneous injection in the test according to Desaulles and Rittel, Memoirs of the Soc. for Endocrinology No. 17 (Cambridge, at the University Press 1968, pages 124–137), the preparation shows a corticotropic action lasting for over 72 hours.

EXAMPLE 13

A suspension of the following composition, homogenised to a particle size of less than 20$\mu$, is prepared as indicated in Example 12:

| | |
|---|---|
| Sesame oil: | 1 ml |
| Benzyl alcohol: | 10 mg |
| Stearate of D-Ser$^1$-Lys$^{17,18}$-$\beta^{1-19}$-corticotropin: | 2 mg |

In the abovementioned test according to Desaulles and Rittel, the preparation, in doses of 0.3 mg/kg administered to rats, shows a duration of action of more than 90 hours.

EXAMPLE 14

A suspension of the following composition, homogenized to a particle size of less than 20$\mu$, is prepared as indicated in Example 12:

| | |
|---|---|
| Groundnut oil: | 1 ml |
| Benzyl alcohol: | 15 mg |
| Stearate of D-Ser$^1$-Lys$^{17,18}$-$\beta^{1-18}$-corticotropin- | |

-continued

Lys¹⁸-amide: 0.3 mg

This single dose is applied, for example, once to twice weekly.

EXAMPLE 15

A suspension of the following composition, homogenised to a particle size of less than 20μ, is prepared as indicated in Example 12 and 13:

| | |
|---|---|
| Groundnut oil: | 1 ml |
| Benzyl alcohol: | 20 mg |
| Stearate of D-Ser¹-Gly³-Lys¹⁷,¹⁸-β¹⁻¹⁸-corticotropin-Lys¹⁸-amide: | 0.1 mg |

EXAMPLE 16

A suspension of the following composition is prepared as in Example 15:

| | |
|---|---|
| Groundnut oil: | 1 ml |
| Benzyl alcohol: | 20 mg |
| Stearate of D-Ser¹-Gly³-Lys¹⁷,¹⁸-β¹⁻¹⁸-corticotropin-Lyshu 18-amide: | 1 mg |

EXAMPLE 17

A suspension of the following composition is prepared as in Example 15:

| | |
|---|---|
| Groundnut oil: | 2 ml |
| Benzyl alcohol: | 20 mg |
| Stearate of D-Ser¹-Gly³-Lys¹⁷,¹⁸-β¹⁻¹⁸-corticotropin-Lys¹⁸-amide: | 1 mg |

EXAMPLE 18

A suspension of the following composition is prepared as in Example 15:

| | |
|---|---|
| Groundnut oil: | 2 ml |
| Benzyl alcohol: | 20 mg |
| Palmitate of D-Ser¹-Lys¹⁷,¹⁸-β¹⁻¹⁸-corticotropin-Lys¹⁸-amide: | 1 mg |

EXAMPLE 19

A suspension of the following composition is prepared as in Example 15:

| | |
|---|---|
| Sesame oil: | 1 ml |
| Benzyl alcohol: | 20 mg |
| Stearate of Synacthen: | 2 mg |

EXAMPLE 20

A suspension of the following composition is prepared as in Example 15:

| | |
|---|---|
| Sesame oil: | 2 ml |
| Benzyl alcohol: | 40 mg |
| Stearate of Synacthen: | 1 mg |

EXAMPLE 21

A suspension of the following composition is prepared as in Example 15:

| | |
|---|---|
| Groundnut oil: | 2 ml |
| Benzyl alcohol: | 20 mg |
| Behenate of Synacthen: | 3 mg |

EXAMPLE 22

A suspension of the following composition is prepared:

| | |
|---|---|
| Physiological sodium chloride solution: | 2 ml |
| Benzyl alcohol: | 20 mg |
| Behenate of Synacthen: | 5 mg |

EXAMPLE 23

A suspension of the following composition is prepared:

| | |
|---|---|
| Physiological sodium chloride solution: | 1 ml |
| Benzyl alcohol: | 10 mg |
| Behenate of Synacthen: | 1.5 mg |

EXAMPLE 24

A suspension of the following composition is prepared:

| | |
|---|---|
| Physiological sodium chloride solution: | 1 ml |
| Benzyl alcohol: | 10 mg |
| Behenate of D-Ser¹-Lys¹⁷,¹⁸-β¹⁻¹⁸-corticotropin-Lys¹⁸-amide | 0.5 mg |

EXAMPLE 25

A suspension of the following composition is prepared:

| | |
|---|---|
| Physiological sodium chloride solution: | 2 ml |
| Benzyl alcohol: | 40 mg |
| Stearate of D-Ser¹-Lys¹⁷,¹⁸-β¹⁻¹⁸-corticotropin-Lys¹⁸-amide: | 2 mg |

EXAMPLE 26

A suspension of the following composition is prepared:

| | |
|---|---|
| Physiological sodium chloride solution: | 2 ml |
| Benzyl alcohol: | 20 mg |
| Behenate of D-Ser¹-Gly³-Lys¹⁷,¹⁸-β¹⁻¹⁸-corticotropin-Lys¹⁸-amide | 1.5 mg |

EXAMPLE 27

A suspension of the following composition is prepared:

| | |
|---|---|
| Physiological sodium chloride solution: | 1 ml |
| Benzyl alcohol: | 10 mg |
| Behenate of D-Ser¹-Gly³-Lys¹⁷,¹⁸-β¹⁻¹⁸-corticotropin-Lys¹⁸-amide: | 0.5 mg |

EXAMPLE 28

A suspension of the following composition is prepared:

| | |
|---|---|
| Physiological sodium chloride solution: | 2 ml |

-continued

| | |
|---|---|
| Benzyl alcohol: | 20 mg |
| Behenate of D-Ser$^1$-Lys$^{17,18}$-β$^{1-19}$-corticotropin | 3 mg |

EXAMPLE 29

A suspension of the following composition is prepared:

| | |
|---|---|
| Physiological sodium chloride solution: | 2 ml |
| Benzyl alcohol: | 20 mg |
| Laurate of D-Ser$^1$-Lys$^{17,18}$-β$^{1-18}$-corticotropin-Lys$^{18}$-amide: | 1.3 mg |

EXAMPLE 30

2.0 ml of an aluminum distearate-groundnut oil gel are warmed to approx. 30°-40°C and mixed with the amount of D-Ser$^1$-Lys$^{17,18}$-β$^{1-18}$-corticotropin-Lys$^{18}$-amide hexastearate corresponding to 6 mg of free peptide. The mixture is diluted to 20.0 ml by adding further gel, whilst stirring, so that 0.3 mg of peptide are present per mg of gel. After filling into ampoules under antimicrobial conditions, the preparation can be administered, for example, 1-2 times weekly.

The gel can be manufactured as follows: 2.0 g of powdered aluminum distearate are added to 100 ml of groundnut oil. This suspension is well mixed and heated to 40°C whilst stirring and warming slowly (2° - 3°C per minute) (at approx. 115°-125°C a clear gel forms). The heating is then switched off and the mixture is further stirred until the temperature has dropped to 120°C. From this temperature downwards, the gel is allowed to cool to room temperature without stirring.

EXAMPLE 31

250 mg of aluminum distearate in 25 ml of benzene are heated to 50°-60°C until a clear colloidal solution has been produced. The amount of D-Ser$^1$-Lys$^{17,18}$-β$^{1-18}$-corticotropin-Lys$^{18}$-amide hexastearate corresponding to 50 mg of free peptide is suspended therein. The suspension is frozen at −70°C and is lyophilized at −10° to −20°C. The lyophilized adsorbate, which has a characteristic structure, is finely ground and suspended in 50 ml of groundnut oil to which 250 mg of phenol are added. The suspension is filled under anti-microbial conditions into ampoules of 1 ml capacity. These contain 1 mg of peptide.

EXAMPLE 32

An amount of D-Ser$^1$-Lys$^{17,18}$-β$^{1-18}$-corticotropin-Lys$^{18}$-amide hexastearate corresponding to 50 mg of free peptide is dissolved in 25 ml of methanol. 250 mg of aluminum distearate which have beforehand been digested several times with methanol are suspended in the solution. The methanol is then distilled off in vacuo at 45°C. The residue is dried in vacuo at 30°-40°C. The very fine adsorbate is suspended in 50 ml of groundnut oil in which 250 mg of phenol have first been dissolved. The suspension is filled under anti-microbial conditions into ampoules of 1 ml capacity. They each contain 1 mg of peptide.

What is claimed is:

1. An injectable pharmaceutical composition comprising an effective amount of an acid addition salt of an ACTH-peptide, said salt being derived from a saturated or unsaturated fatty acid having from 12 to 36 carbon atoms together with a carrier for suspension or solution.

2. The injectable pharmaceutical composition as claimed in claim 1 in the form of an oily suspension.

3. The injectable pharmaceutical composition as claimed in claim 1 in the form of an aqueous suspension.

4. The injectable pharmaceutical composition as claimed in claim 1 comprising an effective amount of an acid addition salt of an ACTH-peptide, said salt being derived from a saturated fatty acid having from 18-22 carbon atoms.

5. The injectable pharmaceutical composition as claimed in claim 1 comprising an effective amount of an acid addition salt of an ACTH-peptide, said salt being derived from behenic acid.

6. The pharmaceutical composition as claimed in claim 15 comprising an effective amount of fatty acid salts of ACTH-peptides, which contain, as ACTH-peptides, peptides or peptide-amides with an N-terminal sequence of up to aminoacid 16 to 39 of the natural corticotropins, wherein optionally one or more of the aminoacids L-serine$^1$ is replaced by D- or L-desamino-serine, glycine, D- or L-(α-alanine), β-alanine, D- or L-proline, D- or L-threonine, propionic acid, butyric acid, caproic acid, ε-aminocaproic acid, D- or L-phenylglycine, D-serine; L-tyrosine$^2$ is replaced by L-phenylalanine; L-serine$^3$ is replaced by glycine or L-alanine; L-methionine$^4$ is replaced by an L-α-amino-lower alkylacetic acid wherein lower alkyl possesses 2-4 carbon atoms; L-glutamic acid$^5$ is replaced by L-glutamine; L-lysine in positions 11 and/or 15 and 16 is replaced by L-ornithine; L-arginine$^{17,18}$ is replaced by L-lysine or L-ornithine; aminoacid$^{25}$ is replaced by L-valine and/or one or more of the aminoacids 1-4 of the sequence ar missing.

7. The pharmaceutical composition as claimed in claim 1 comprising an effective amount of fatty acid salts of ACTH-peptides, which contain, as ACTH-peptides, peptides or peptide-amides with a sequence of 18-24, preferably 18-19, aminoacids from the amino end of the corticotropins, wherein optionally one or more of the aminoacids L-serine$^1$ is replaced by D- or L-desamino-serine, glycine, D- or L-(α-alanine), β-alanine, D- or L-proline, D- or L-threonine, propionic acid, butyric acid, caproic acid, ε-aminocaproic acid, D- or L-phenylglycine, D-serine; L-tyrosine$^2$ is replaced by L-phenylalanine; L-serine$^3$ is replaced by glycine or L-alanine; L-methionine$^4$ is replaced by an L-α-amino-lower alkylacetic acid wherein lower alkyl possesses 2-4 carbon atoms; L-glutamic acid$^5$ is replaced by L-glutamine; L-lysine in positions 11 and/or 15 and 16 is replaced by L-ornithine; L-arginine$^{17,18}$ is replaced by L-lysine or L-ornithine; aminoacid$^{25}$ is replaced by L-valine.

8. The pharmaceutical composition as claimed in claim 1 comprising an effective amount of fatty acid salts of ACTH-peptides, which contain, as ACTH-peptides, peptides or peptideamides with a sequence of 18-39 aminoacids, wherein the first aminoacid is an aminoacid with the D-configuration, above all, D-serine.

9. The pharmaceutical composition as claimed in claim 1 comprising an effective amount of fatty acid salts of ACTH-peptides which contain D-Ser$^1$-Lys$^{17,18}$-β$^{1-18}$-corticotropin-Lys$^{18}$-amide as the ACTH-peptide.

10. The pharmaceutical composition as claimed in claim 1 comprising an effective amount of fatty acid salts of ACTH-peptides which contain D-Ser$^1$-Gly$^3$-Lys$^{17,18}$-$\beta^{1-18}$-corticotropin-Lys$^{18}$-amide as the ACTH-peptide.

11. The pharmaceutical composition as claimed in claim 1 comprising an effective amount of fatty acid salts of ACTH-peptides which contain D-Ser$^1$-Lys$^{17,18}$-$\beta^{1-19}$-corticotropin or its C-terminal amide as the ACTH-peptide.

12. The pharmaceutical composition as claimed in claim 1 comprising an effective amount of fatty acid salts of ACTH-peptides which contain $\beta^{1-24}$-corticotropin or its C-terminal amide as the ACTH-peptide.

13. The pharmaceutical composition of claim 1, wherein the fatty acid salt of an ACTH-peptide is the behenetate of ACTH-peptides.

* * * * *